United States Patent
Hubbell et al.

(10) Patent No.: US 6,289,725 B1
(45) Date of Patent: Sep. 18, 2001

(54) FIELD MATRIC POTENTIAL SENSOR (75) Inventors: Joel M. Hubbell; James B. Sisson, both of Idaho Falls, ID (US)

(73) Assignee: Bechtel BWXT Idaho, LLC, Idaho Falls, ID (US)

( * ) Notice: Subject to any disclaimer, the term of this patent is extended or adjusted under 35 U.S.C. 154(b) by 0 days.

(21) Appl. No.: 09/070,825

(22) Filed: Apr. 30, 1998

(51) Int. Cl.[7] .................................................. G01N 15/08
(52) U.S. Cl. ..................................... 73/73; 73/38; 141/47
(58) Field of Search ................... 73/73, 76, 38; 141/47

(56) References Cited

U.S. PATENT DOCUMENTS

| | | | |
|---|---|---|---|
| 3,898,872 | 8/1975 | Skaling et al. | 73/73 |
| 4,068,525 | 1/1978 | Skaling et al. | 73/73 |
| 4,137,931 | 2/1979 | Hasenbeck | 73/73 |
| 4,310,758 | * 1/1982 | Peterson | 250/255 |
| 4,520,657 | 6/1985 | Marthaler | 73/73 |
| 4,655,076 | * 4/1987 | Weihe et al. | 73/73 |
| 4,679,422 | * 7/1987 | Rubin et al. | 73/38 |
| 4,922,945 | * 5/1990 | Browne | 73/73 |
| 5,113,888 | * 5/1992 | Beggs | 137/1 |
| 5,420,517 | 5/1995 | Skaling et al. | 73/73 |
| 5,644,947 | 7/1997 | Hubbell et al. | 73/73 |
| 5,646,537 | 7/1997 | Skaling et al. | 73/73 |
| 5,789,662 | * 8/1998 | Dayal | 73/38 |
| 5,941,121 | * 8/1999 | Faybishenko | 73/73 |
| 6,055,850 | * 5/2000 | Turner et al. | 73/38 |

OTHER PUBLICATIONS

Nimmo, Jr; Miller, R. E. Soil Science Soc. of Amer. J. v 50, n 5, Sep.–Oct. 1986, p 1105–1113.*

Tokunaga, T.K. Water Resources Research v 33, n 6, Jun. 1997, p 1509–1513.*

* cited by examiner

Primary Examiner—Hezron Williams
Assistant Examiner—Michael Cygan
(74) Attorney, Agent, or Firm—Wells St John Roberts Gregory & Matkin (57) ABSTRACT

A method of determining matric potential of a sample, the method comprising placing the sample in a container, the container having an opening; and contacting the sample with a tensiometer via the opening. An apparatus for determining matric potential of a sample, the apparatus comprising a housing configured to receive a sample; a portable matric potential sensing device extending into the housing and having a porous member; and a wall closing the housing to insulate the sample and at least a portion of the matric potential sensing device including the porous member.

28 Claims, 5 Drawing Sheets

FIELD MATRIC POTENTIAL SENSOR

CONTRACTUAL ORIGIN OF THE INVENTION

The United States Government has rights in this invention disclosed under contract number DE-AC07-76ID01570 between the U.S. Department of Energy and EG&G Idaho, Inc., now contract number DE-AC07-94ID13223 with Lockheed Martin Idaho Technologies Company.

TECHNICAL FIELD

The invention relates to soil matric potential, soil water potential, or soil moisture tension. More particularly, the invention relates to methods and apparatus for determining soil moisture potential.

BACKGROUND OF THE INVENTION

Methods and apparatus for determining soil matric potential are known in the art. Soil matric potential (soil water potential) is soil moisture tension, an indicator of the ability of water to move within soil.

Tensiometers have been used in the past for soil moisture measurement. Tensiometers measure how tightly water is being held by soil. See, for example, U.S. Pat. No. 3,898,872 to Skaling et al. (incorporated herein by reference). The tensiometer disclosed in the Skaling et al. patent includes a liquid filled vessel having walls with a porous section to be placed in the soil. Pressure in the tube is measured to determine the moisture content of the soil. Another tensiometer is described in commonly assigned U.S. Pat. No. 5,644,947 to Hubbell et al. (incorporated herein by reference).

A conduction type soil matric potential sensor is disclosed in U.S. Pat. No. 4,137,931 to Hasenbeck (incorporated herein by reference). The Hasenbeck patent discloses a matric potential sensor including a housing having a porous wall adapted to be located underground, and spaced electrodes carried in the housing and coupled to a source of electrical current. Current flow varies as a function of moisture content of soil. Moisture content varies as a function of the matric potential of the soil surrounding the housing in response to moisture transmission through the porous housing into the surrounding soil.

Apparatus for measuring matric potential are typically buried in the ground. Sediment samples are routinely collected, for characterization activities, at construction sites, dam sites, landfills, hazardous waste disposal sites, and other sites. The samples are collected by drilling or by other means. These sediment samples are often tested for moisture content, but typically not for matric potential. When such samples are tested for matric potential, they may be tested for matric potential in the dry range using a thermocouple psychrometer. Thermocouple psychrometers are used in the laboratory to calculate matric potential by using the Peltier Effect of adiabatic cooling to determine humidity, and then relating the determined humidity to calculate matric potential. Thermocouple psychrometers require considerable skills to maintain calibration, and therefore generally yield poor results.

BRIEF DESCRIPTION OF THE DRAWINGS

Preferred embodiments of the invention are described below with reference to the accompanying drawings, which are briefly described below.

SUMMARY OF THE INVENTION

The invention provides a method of determining matric potential of a sample. The method comprises placing the sample in a container, the container having an opening; and contacting the sample with a tensiometer via the opening.

In one aspect of the invention, a method of determining matric potential of a sample comprises supporting the sample on a surface in a housing. The top of the sample is contacted with a portable matric potential sensing device having a porous member. The housing is closed to insulate the sample and at least a portion of the matric potential sensing device including the porous member.

In another aspect of the invention, a method of determining matric potential of a sample comprises providing a tensiometer including a porous member, a fluid chamber above the porous member and in fluid communication with the porous member, and a pressure transducer in fluid communication with the fluid chamber. The chamber is filled with liquid. The sample is placed in a container having an open top. The top surface of the sample is contacted with the porous member via the open top. The container, sample, and at least a portion of the tensiometer which includes the porous member are insulated against the ambient temperature and to minimize evaporation of water from the sample. The pressure in the fluid chamber is adjusted, by changing the volume of the fluid chamber, to speed equilibration between pressure in the fluid chamber and pressure in the sample.

One aspect of the invention provides an apparatus for determining the matric potential of a sample. The apparatus comprises a container configured to receive the sample, the container having an opening. The apparatus further comprise a tensiometer configured to contact the sample via the opening, the tensiometer including a porous member. The apparatus further comprises a portable insulator configured to insulate the container, the sample, and at least a portion of the tensiometer including the porous member, against the ambient temperature.

In another aspect of the invention, an apparatus for determining matric potential of a sample comprises a housing configured to receive a sample. A portable matric potential sensing device extends into the housing and has a porous member. A wall closes the housing to insulate the sample and at least a portion of the matric potential sensing device including the porous member.

In another aspect of the invention, an apparatus for determining matric potential of a sample comprises a tensiometer including a porous member, including a fluid chamber above the porous member and in fluid communication with the porous member, and including a pressure transducer in fluid communication with the fluid chamber. A container has an open top and is configured to receive a sample. The container is positioned relative to the tensiometer such that the sample can be contacted by the porous member via the open top. An insulator insulates the container, and at least a portion of the tensiometer which includes the porous member, against the ambient temperature. A pressure adjustment mechanism is configured to adjust the pressure in the fluid chamber, by changing the volume of the fluid chamber, to speed equilibration between pressure in the fluid chamber and pressure in the sample.

One aspect of the invention relates to methods of an apparatus for easily measuring matric potential from small samples on site, without the need for burying an apparatus, and without need for a thermocouple psychrometer. Further, thermocouple psychrometers measure over a different, much dryer range than tensiometers. A method and apparatus is provided for determining matric potential or soil moisture tension from a sample, such as a sediment sample. The sample is collected by drilling or other means. In one embodiment, a portable tensiometer is employed. In another embodiment, a heat dissipation sensor is employed. Other matric potential sensors can be employed. The sample is placed in a sample container, and the matric potential sensor is placed in contact with the sample. The matric potential sensor is allowed to equilibrate for a predetermined amount of time under isothermal conditions prior to taking a reading with the sensor. A reading is then taken and recorded. These readings are more useful than moisture content readings that are typically taken because the driving force for water movement is soil water potential, not moisture content.

DETAILED DESCRIPTION OF THE PREFERRED EMBODIMENTS

This disclosure of the invention is submitted in furtherance of the constitutional purposes of the U.S. Patent Laws "to promote the progress of science and useful arts (Article 1, Section 8).

Figure 1:
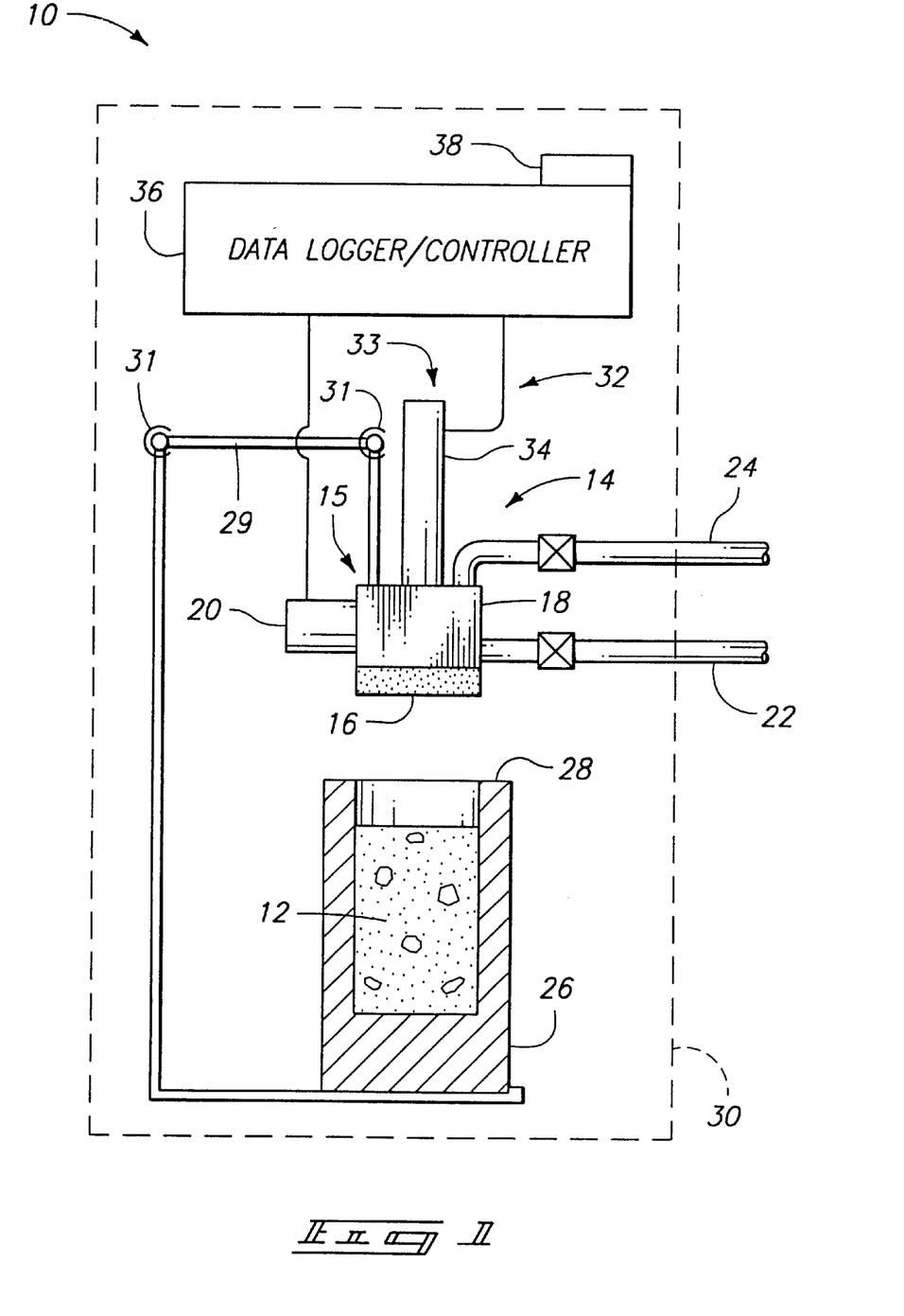
FIG. 1 is a diagrammatical illustration of an apparatus for determining matric potential of a sample, using a tensiometer, in accordance with one aspect of the invention.

FIG. 1 shows an apparatus 10 for field determination of matric potential of a sample 12. The apparatus 10 may be used, for example, at construction sites, dam sites, landfills, hazardous waste disposal sites, or other sites remote from a lab. The sample 12 may be soil, sediment, or permeable rock obtained by drilling, digging, or other means.

The apparatus 10 includes a portable tensiometer 14. Tensiometers are known in the art. See, for example, U.S. Pat. No. 5,644,947 to Hubbell et al. and U.S. Pat. No. 3,898,872 to Skaling, both of which are incorporated herein by reference. The tensiometer 14 includes a body 15 comprising a porous member or plate 16. The tensiometer 14 further includes a fluid chamber 18 above the porous member 16 and in fluid communication with the porous member 16. The tensiometer 14 further includes a pressure transducer 20 in fluid communication with the fluid chamber 18. The pressure transducer 20 measures pressure in the fluid chamber 18. Water is held in soil under tension. The porous member 16 of the tensiometer 14 is semi-permeable allowing water to move freely but not air. Water from the fluid chamber 18 is withdrawn out of the porous member 16 into the sample 12 until water pressure in the fluid chamber 18 equals water pressure in the sample 12. The porous member 16 impedes air from moving between the fluid chamber 18 and the sample 12 but permits water to move between the fluid chamber 18 and the sample 12.

In the embodiment shown in FIG. 1, the tensiometer 14 further includes a water fill tube 22 in fluid communication with the fluid chamber 18. The water fill tube 22 is used for adding water to the fluid chamber 18 to keep the fluid chamber 18 filled and the porous member 16 saturated during use. The tensiometer 14 further includes a deairing tube 24 in fluid communication with the top of the fluid chamber 18. The deairing tube is used to remove air bubbles that rise in the fluid chamber. The fluid chamber 18 is fluidly sealed but for the porous member 16 and water fill and deairing tubes.

The apparatus 10 further includes a portable holder or container 26 having an open top 28 and configured to receive sample 12. The container 26 is positioned relative to the tensiometer 14 such that the sample 12 can be contacted by the porous member 16 via the open top 28. Preferably, the sample 12 is not filled to the top 28 of the container so less moisture is lost to air. The container 26 is movable relative to the tensiometer 14. For example, in the illustrated embodiment, the tensiometer 14 is supported relative to the container 26 with a mechanism 29 similar to a mechanism found on lamps having movable arms. The mechanism 29 includes for example, arms including pivots 31 permitting movement of the tensiometer 14 towards and away from the container 26.

Figure 2:
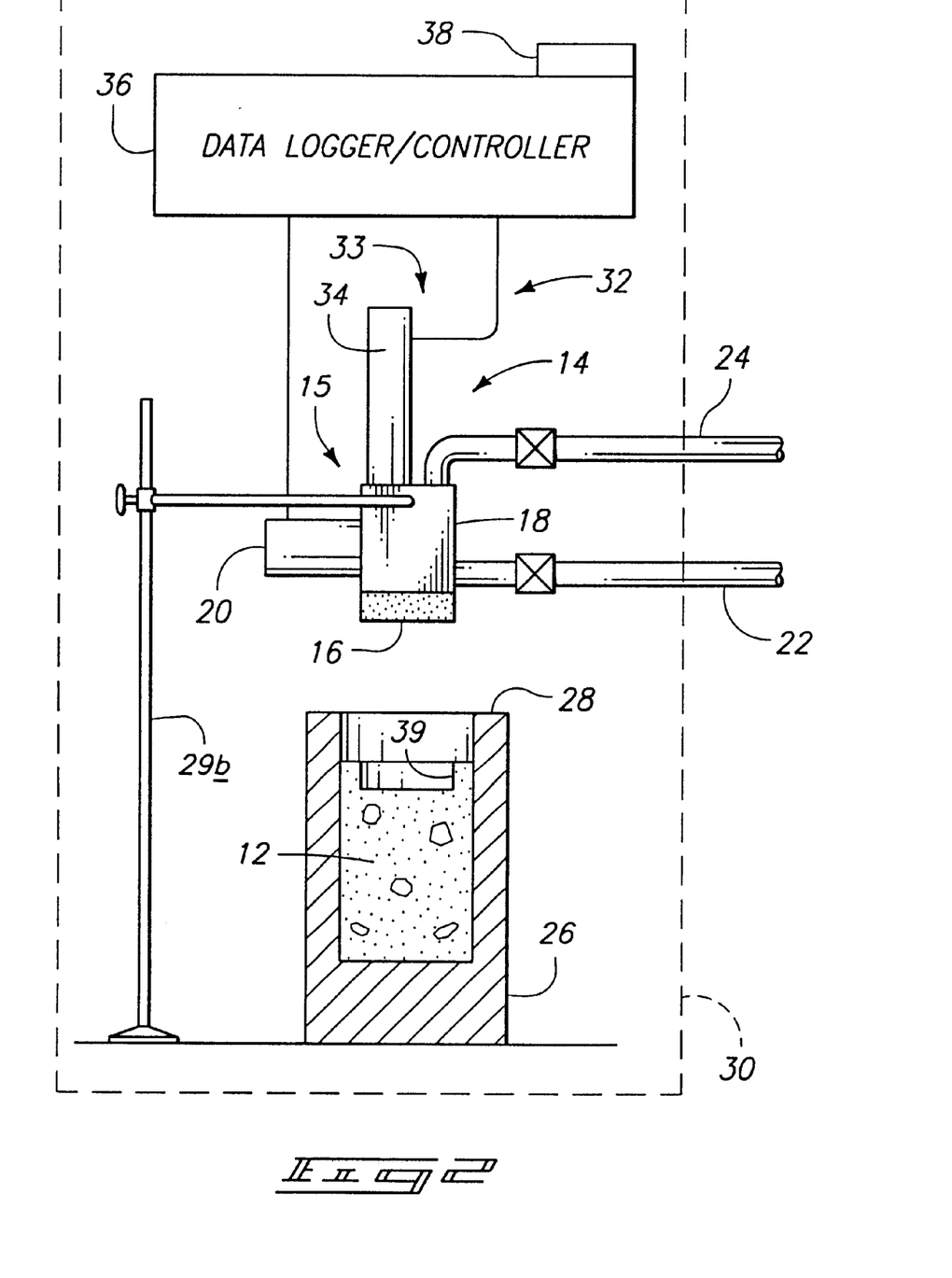
FIG. 2 is a diagrammatical illustration of an apparatus for determining matric potential of a sample, using a tensiometer, in accordance with one aspect of the invention.

In an alternative embodiment shown in FIG. 2, like reference numerals indicating like components, the tensiometer 14 is supported relative to the container 26 with a mechanism 29B that includes an arm slidable relative to a rod so that the tensiometer 14 slides down under the force of gravity. The sample may be bored out, as shown in FIG. 2, for receipt of the tensiometer 14 fit into the bore 39. In one embodiment, a weight (not shown) is added to the tensiometer to push down the tensiometer against the sample. The mechanism 29 or 29B can be omitted. If the mechanism 29 or 29B is omitted, the tensiometer is placed against the sample and held by gravity.

The apparatus 10 further includes (FIGS. 1 and 2) a portable housing or insulator 30 insulating the container 26, the sample 12, and at least a portion of the tensiometer 14 which includes the porous member 16, against the ambient temperature. In the embodiment shown in FIG. 1, the insulator 30 insulates the entire tensiometer 14 against the ambient temperature. The insulator 30 can be made of any appropriate material, or combination of materials, such as plastic, double panes of glass or other material with a vacuum created between the double panes, polyurethane, or material such as the material used to manufacture coolers. In one embodiment (not shown), the container 26 is omitted and the sample is merely placed on a surface in the housing 30.

The apparatus 10 further includes a pressure adjustment mechanism 32 configured to adjust the pressure in the fluid chamber 18. In the embodiment of FIG. 1, the pressure adjustment mechanism adjusts the pressure in the fluid chamber by changing the volume of the fluid chamber 18. This speeds equilibration between pressure in the fluid chamber and pressure in the sample. In the embodiment shown in FIG. 1, the pressure adjustment mechanism 32 comprises a piston assembly 33 including a piston 34 movable relative to a cylinder (not shown) partly defining the fluid chamber 18 to change the pressure in the fluid chamber 18. Movement of the piston 34 in the direction into the fluid chamber 18 increases pressure in the fluid chamber 18, and movement of the piston 34 in the direction out of the fluid chamber 18 decreases pressure in the fluid chamber 18, in a manner similar to operation of a syringe. In one embodiment, the piston 34 moves in response to rate of change of pressure in the fluid chamber 18.

The apparatus 10 further includes a data logger 36 electrically connected to the pressure transducer 20 and either displaying or periodically recording readings measured by the pressure transducer 20. In the illustrated embodiment, the data logger 36 includes a display 38. In the embodiment where the piston 34 moves in response to rate of change of pressure in the fluid chamber 18, the data logger 36 is electrically connected to the piston assembly 33 and controls movement of the piston 34 (e.g., by controlling a motor driving the piston). If pressure is falling rapidly in the fluid chamber 18 (e.g., at a rate faster than a predetermined rate), the data logger 36 effects movement of the piston 34 out of the fluid chamber 18 to further decrease pressure. A bisection method is employed to determine when equilibrium has been attained within desired predetermined limits. Bisection methods are known in the art.

Figure 3:
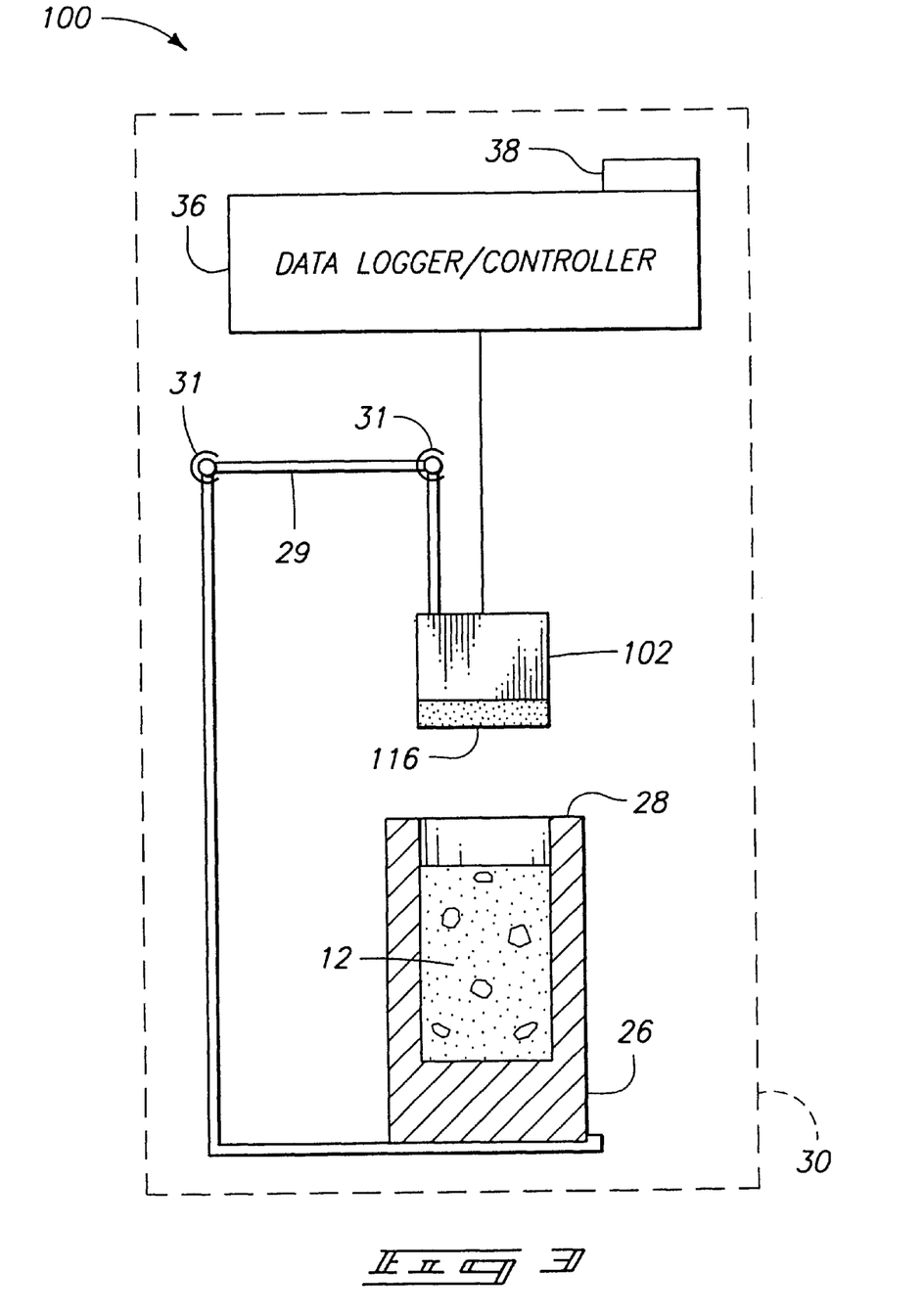
FIG. 3 is a diagrammatical illustration of an apparatus for determining matric potential of a sample, using a heat dissipation sensor, in accordance with another aspect of the invention.

FIG. 3 shows an apparatus 100 for determining matric potential of a sample, in accordance with an alternative embodiment of the invention. The apparatus 100 is similar to the apparatus 10, like reference numerals indicating like components, except that the apparatus 100 includes a heat dissipation sensor 102 instead of a tensiometer. The apparatus 100 includes a porous member 116 like the porous member 16 of the apparatus 10. The porous member 116 is made of porous ceramic or porcelain material that contains a heater.

In operation, the porous member 116 is placed into contact with a sample 28. Pulses of energy are supplied to the heater. Temperature pulses dissipate slower if the porous member 116 is dry than if the porous member 116 is wet. Over time, water potential in the porous member 116 and water in the sample 28 equilibrate to the same pressure. Different pressures have different temperature responses. The temperature responses are followed with a transducer 120 to determine pressure. Heat dissipation sensors are commercially available, for example, from Campbell Scientific.

Tensiometers are limited to being able to determine matric potential up to approximately 0.8 or 0.9 bar tension (800–900 cm water). On the other hand, apparatus employing heat dissipation sensors can be used to determine matric potential of sample having up to approximately one hundred bar tension.

Figure 4:
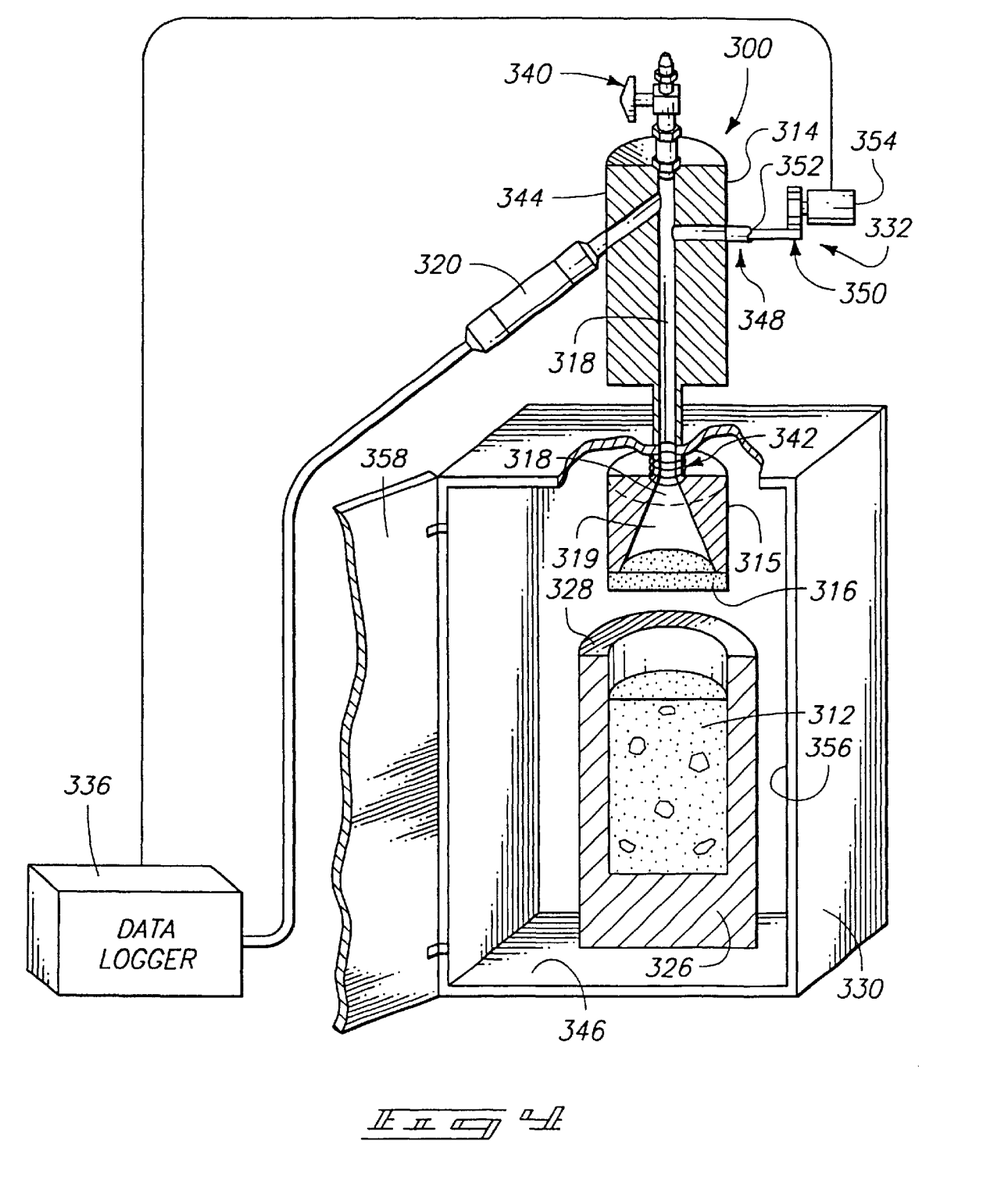
FIG. 4 is a perspective view of an apparatus for determining matric potential of a sample, using a tensiometer, in accordance with an alternative embodiment of the invention.

FIG. 4 is a perspective view of an apparatus 300 for determining matric potential of a sample, in accordance with an alternative embodiment of the invention.

The apparatus 300 includes a portable tensiometer 314. The tensiometer 314 includes a body 315 comprising a porous member or plate 316. The tensiometer 314 further includes a fluid chamber 318 above the porous member 316 and in fluid communication with the porous member 316. The tensiometer 314 further includes a pressure transducer 320 in fluid communication with the fluid chamber 318. The pressure transducer 320 measures pressure in the fluid chamber 318. In the embodiment shown in FIG. 4, the fluid chamber includes a portion 319 tapered inwardly in a direction upward from the porous member (e.g., in the shape of an inverted funnel). The fluid chamber 318 is fluidly sealed, in operation, but for the porous member 316. Water is held in soil under tension. The porous member 316 of the tensiometer 314 is semi-permeable allowing water to move freely but not air. Water from the fluid chamber 318 is withdrawn from the porous member 316 into the sample 312 until water pressure in the fluid chamber 318 equals water pressure in the sample 312. The porous member 316 impedes air from moving between the fluid chamber 318 and the sample 312 but permits water to move between the fluid chamber 318 and the sample 312.

In the embodiment shown in FIG. 4, the tensiometer 314 further includes a valve 340 in fluid communication with the fluid chamber 318. The valve 340 is used for adding water to the fluid chamber 318 and to remove air bubbles that rise in the fluid chamber, as necessary. The valve 340 is used instead of the water fill and deairing tubes of the embodiment of FIG. 1.

The apparatus 300 further includes a portable holder or container 326 having an open top 328 and configured to receive sample 312. The container 326 is positioned relative to the tensiometer 314 such that the sample 312 can be contacted by the porous member 316 via the open top 328. The container 326 is movable relative to the tensiometer 314. For example, in the illustrated embodiment, the tensiometer 314 includes a head 344 defining the water chamber together with the body 315, and a spring 342 between the body 315 and the head 344. The spring 342 biases the porous member 316 toward the top surface of the sample 312. In one embodiment, the spring 342 includes a hollow, closed, interior portion defining part of the fluid chamber 318. In an alternative embodiment, a hose or tube (not shown), surrounded by the spring 342, fluidly connects the portion of the fluid chamber 318 in the head 344 to the portion of the fluid chamber 318 in the body 315. After the porous member 316 comes in contact with the sample 312, there are several ways to make the connection without allowing the water in the sample 312 or the porous member 316 to evaporate (thereby giving dryer measurements). For example, a flexible impermeable film such as Saran wrap (TM) or parafilm can be used to wrap the connection. Alternatively, the sample holder 326 can recess the soil (have an indentation in the end 328), or the sample can be dug out to some given depth.

The apparatus 300 further includes a portable housing or insulator 330 insulating the container 326, the sample 312, and at least a portion of the tensiometer 314 which includes the porous member 316, against the ambient temperature. In the embodiment shown in FIG. 3, the insulator 330 insulates only the body 315 of the tensiometer 314 against the ambient temperature. More particularly, the insulator 330 has an aperture passing the spring 342 and the portion of the fluid chamber 318 extending between the head 344 and the body 315. The insulator 330 can be made of any appropriate material, or combination of materials, such as plastic, double panes of glass or other material with a vacuum created between the double panes, polyurethane, or material such as the material used to manufacture coolers. The insulator 330 can be in any desired shape. In one embodiment (not shown), the container 326 is omitted and the sample is merely placed on a surface 346 in the housing 330. The housing 330 includes a chamber 356 and a door 358 selectively opening or closing the chamber 356.

The apparatus 300 further includes a pressure adjustment mechanism 332 configured to adjust the pressure in the fluid chamber 318. In the embodiment of FIG. 1, the pressure adjustment mechanism adjusts the pressure in the fluid chamber by changing the volume of the fluid chamber 318. This speeds equilibration between pressure in the fluid chamber and pressure in the sample. In the embodiment shown in FIG. 1, the pressure adjustment mechanism 332 comprises a null point valve 348 including a manual screw-in type piston 350 movable relative to a cylinder 352. The cylinder 352 partly defines the fluid chamber 318. Screwing in or out of the piston 350 relative to the cylinder 352 changes the pressure in the fluid chamber 318. Movement of the piston 350 in the direction into the cylinder 352 increases pressure in the fluid chamber 318, and movement of the piston 350 in the direction out of the fluid chamber 318 decreases pressure in the fluid chamber 318. In one embodiment, the piston 334 is driven by a motor 354 or other servo mechanism and moves in response to rate of change of pressure in the fluid chamber 318.

The apparatus 300 further includes a data logger 336 electrically connected to the pressure transducer 320 and either displaying or periodically recording readings measured by the pressure transducer 320. In the embodiment where the piston 350 moves in response to rate of change of pressure in the fluid chamber 318, the data logger 336 is electrically connected to the motor 354 and controls movement of the piston 350 (e.g., by controlling the motor 354 driving the piston). If pressure is falling rapidly in the fluid chamber 318, the data logger 336 effects movement of the piston 350 out of the fluid chamber 318 to decrease pressure. A bisection method is employed to determine when equilibrium has been attained within desired predetermined limits. Bisection methods are known in the art.

In operation, the fluid chamber 318 is filled with a liquid (e.g., water), and air bubbles are removed, using the ball valve 340. The sample 312 is placed in the container 326. A top surface of the sample 312 is contacted with the porous member 316 via the open top 328 of the container 326. The container 326, sample 312, and at least a portion of the tensiometer 314 which includes the porous member 316 are insulated against the ambient temperature, such as by closing the door 358 of the housing 330. The pressure in the fluid chamber 318 is adjusted, by changing the volume of the fluid chamber 318; e.g., to speed equilibration between pressure in the fluid chamber 318 and pressure in the sample 312. After equilibration is reached, a reading is taken and recorded by the data logger 336.

Figure 5:
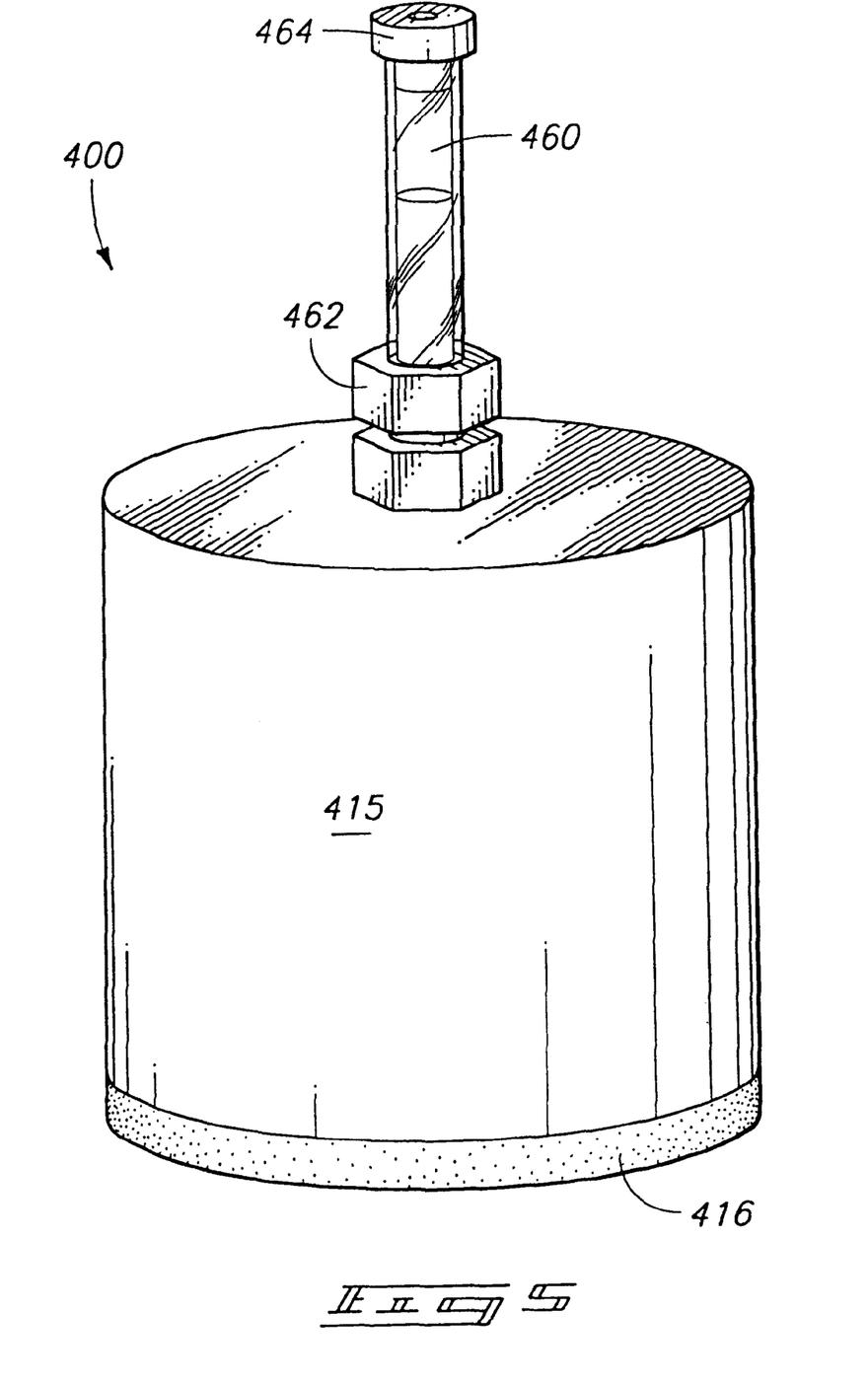
FIG. 5 is a perspective view of a simple apparatus for determining matric potential of a sample.

FIG. 5 is a perspective view of an apparatus 400 for determining matric potential of a sample, in accordance with another alternative embodiment of the invention. The apparatus 400 is substantially similar to the lower portion or body 315 of the apparatus 300 shown in FIG. 4. The apparatus 400 is a simple portable tensiometer. The tensiometer 400 includes a body 415 comprising a porous member or plate 416. The tensiometer 400 further includes a fluid chamber (not shown) above the porous member 416 and in fluid communication with the porous member 416. The fluid chamber is substantially similar to the fluid chamber 319 of the apparatus 400 FIG. 4. The tensiometer 400 further includes tubing 460 formed of acrylic or other appropriate material conventionally used for tubing, and having opposite open ends. The tubing 460 is preferably clear or opaque. The tensiometer 400 further includes a connector 462 coupling one open end of the tubing 460 to the fluid chamber, and a septum 464 on the other end of the tubing 460. The fluid chamber is fluidly sealed, in operation, but for the porous member 416. Water is held in soil under tension. The porous member 416 of the tensiometer 314 is semi-permeable allowing water to move freely but not air. Water from the fluid chamber is withdrawn from the porous member 416 into a sample until water pressure in the fluid chamber equals water pressure in the sample. A pressure gauge such as presented in U.S. Pat. No. 4,520,657 (incorporated herein by reference) can be used to record the pressure in the tensiometer. A standard Bourdon type pressure gauge can also be used. In use, the porous member 416 is placed on top of a sample (e.g., a sediment sample) and then a flexible impermeable film such as Saran wrap (TM) or parafilm is wrapped around the body and sample.

In the past, there was a belief that intimate contact was needed between a tensiometer and a sample. Thus, in the past, bores were drilled for insertion of a tensiometer. By investigation, the inventors have determined that only contact with the top of a sample is necessary. By practicing the invention, matric potential of a sample can be determined on-site, providing quick readings. Thus, time and money is saved and accurate readings can be obtained.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A portable tensiometer, comprising:
   a porous member configured to contact a surface of a sample;
   a fluid chamber in fluid communication with the porous member;
   a pressure transducer in fluid communication with the fluid chamber;
   tubing having opposite open ends;
   a connector coupling one of the open ends of the tubing to the fluid chamber; and
   a septum on the other end of the tubing.

2. A method of determining matric potential of a sample, the method comprising:
   placing the sample in a container, the container having an opening, such that an upper surface of the sample is accessible via the opening;
   providing a tensiometer including a porous plate, a fluid chamber above the porous plate and in fluid communication with the porous plate, and a pressure transducer in fluid communication with the fluid chamber;
   providing a mechanism supporting the tensiometer for selective movement of the porous plate toward and away from the opening of the container when the container is in a sampling position;
   contacting the upper surface of the sample with the porous plate of a tensiometer via the opening, without burying the tensiometer in the sample; and
   determining pressure in the tensiometer after water pressure in the fluid chamber has generally equalized to water pressure in the sample.

3. A method of determining matric potential of a sample in accordance with claim 2 wherein contacting the sample with the tensiometer comprises contacting the sample with the porous plate, the method further comprising insulating the container, sample, and at least a portion of the tensiometer including the porous plate, against the ambient.

4. A method of determining matric potential of a sample in accordance with claim 2, the method further comprising encasing the container, the sample, and the porous plate in a housing.

5. A method of determining matric potential of a sample in accordance with claim 2 wherein the tensiometer includes a body comprising the porous plate and a fluid chamber, the fluid chamber being in fluid communication with the porous plate, wherein the method further comprises adjusting the pressure in the fluid chamber to speed equilibration between pressure in the fluid chamber and pressure in the sample.

6. A method of determining matric potential of a sample in accordance with claim 5 wherein the fluid chamber, in operation, is fluidically sealed but for the porous plate.

7. A method of determining matric potential of a sample in accordance with claim 5 wherein the pressure in the fluid chamber is adjusted in response to rate of change of pressure in the fluid chamber.

8. A method of determining matric potential of a sample in accordance with claim 2 wherein the tensiometer includes a body comprising the porous plate and a fluid chamber, the fluid chamber being in fluid communication with the porous plate, the method further comprising de-airing the fluid chamber.

9. A method of determining matric potential of a sample, the method comprising:
supporting the sample on a surface in a housing;
providing a matric potential sensing device including a porous plate, a fluid chamber above the porous plate and in fluid communication with the porous plate, a pressure transducer in fluid communication with the fluid chamber;
providing a mechanism to support the tensiometer for movement of the porous plate toward and away from the surface in the housing;
contacting the top of the sample with the porous plate of the portable matric potential sensing device; and
closing the housing to insulate the sample and at least a portion of the matric potential sensing device including the porous member.

10. A method of determining matric potential of a sample in accordance with claim 9 wherein the contacting comprises employing a portable tensiometer.

11. An apparatus for determining matric potential, the apparatus comprising:
a tensiometer including:
a porous member configured to contact an upper surface of a sample;
a fluid chamber above the porous member and in fluid communication with the porous member;
a pressure transducer in fluid communication with the fluid chamber;
a water fill tube in fluid communication with the fluid chamber; and
a deairing tube in fluid communication with the fluid chamber;
a portable container movable to and from a sampling position where the top of the sample can be contacted by the porous member, and having an open top configured to receive the sample; and
a mechanism supporting the tensiometer for movement of the porous member toward and away from the open end of the portable container when the container is in the sampling position.

12. A method of determining matric potential of a sample, the method comprising:
providing a tensiometer including a porous member, a fluid chamber above the porous member and in fluid communication with the porous member, and a pressure transducer in fluid communication with the fluid chamber, and providing a mechanism to support the tensiometer for movement of the porous member toward and away from a predetermined location;
filling the chamber with a liquid;
placing the sample in a container having an open top, the container being located at the predetermined location;
contacting the sample with the porous member via the open top;
insulating the container, sample, and at least a portion of the tensiometer which includes the porous member against the ambient temperature; and
adjusting the pressure in the fluid chamber, by changing the volume of the fluid chamber, to speed equilibration between pressure in the fluid chamber and pressure in the sample.

13. A method of determining matric potential of a sample in accordance with claim 12 and further comprising reading the pressure in the fluid chamber with the pressure transducer after equilibration has been reached.

14. An apparatus for determining the matric potential of a sample, the apparatus comprising:
a container configured to receive the sample, the container having an opening;
a tensiometer including a body having a porous member and a fluid chamber in fluid communication with the porous member, the porous member being configured to contact a top surface of the sample via the opening, the tensiometer further including a pressure transducer in fluid communication with the fluid chamber, and a pressure adjustment mechanism in the fluid chamber to adjust pressure in the fluid chamber;
a mechanism supporting the tensiometer for selective movement of the porous member toward and away from the opening of the container; and
an insulator configured to insulate the container, the sample, and at least a portion of the tensiometer including the porous member, against the ambient temperature.

15. An apparatus for determining the matric potential of a sample in accordance with claim 14 wherein the fluid chamber includes a portion tapered inwardly in a direction upward from the porous member.

16. An apparatus for determining the matric potential of a sample in accordance with claim 14 wherein the fluid chamber, in operation, is fluidically sealed but for the porous member.

17. An apparatus for determining the matric potential of a sample in accordance with claim 14 and further including means for adjusting the pressure in the fluid chamber in response to rate of change of pressure in the fluid chamber.

18. An apparatus for determining the matric potential of a sample in accordance with claim 14 and further including a piston movable relative to the fluid chamber to change the pressure in the fluid chamber, the piston moving in response to rate of change of pressure in the fluid chamber.

19. An apparatus for determining matric potential of a sample, the apparatus comprising:
a tensiometer including a porous member configured to contact an upper surface of a sample, including a fluid chamber above the porous member and in fluid communication with the porous member, and including a pressure transducer in fluid communication with the fluid chamber;
a container having an open top and configured to receive a sample, the container being positioned relative to the tensiometer such that the upper surface of the sample can be contacted by the porous member via the open top;
a mechanism to support the tensiometer for selective movement of the porous member toward and away from the open top of the container;
an insulator insulating the container, and at least a portion of the tensiometer which includes the porous member, against the ambient temperature, and
a pressure adjustment mechanism configured to adjust the pressure in the fluid chamber, by changing the volume of the fluid chamber, to speed equilibration between pressure in the fluid chamber and pressure in the sample.

20. An apparatus for determining matric potential of a sample method in accordance with claim 19 and further comprising a piston movable relative to the fluid chamber to change the pressure in the fluid chamber, the piston moving in response to rate of change of pressure in the fluid chamber.

21. A portable tensiometer, comprising:

a porous member configured to contact an upper surface of a sample;

a fluid chamber above the porous member and in fluid communication with the porous member;

a pressure transducer in fluid communication with the fluid chamber;

tubing having opposite open ends;

a connector coupling one of the open ends of the tubing to the fluid chamber; and a septum on the other end of the tubing.

22. An apparatus for determining matric potential, the apparatus comprising:

a tensiometer including:
  a porous member configured to contact an upper surface of a sample;
  a fluid chamber above the porous member and in fluid communication with the porous member;
  a pressure transducer in fluid communication with the fluid chamber;
  a water fill tube in fluid communication with the fluid chamber; and
  a deairing tube in fluid communication with the fluid chamber;

a portable container movable to and from a sampling position where the top of the sample can be contacted by the porous member, and having an open top configured to receive the sample;

a mechanism supporting the tensiometer for movement of the porous member toward and away from the open end of the portable container when the container is in the sampling position; and a data logger electrically coupled to the pressure transducer and configured to record a reading measured by the pressure transducer.

23. A portable tensiometer in accordance with claim 21 wherein the fluid chamber is fluidically sealed, but for the porous plate, tubing, and septum.

24. A portable tensiometer in accordance with claim 21 wherein the tubing is clear.

25. A portable tensiometer in accordance with claim 21 wherein the tubing is opaque.

26. A portable tensiometer in accordance with claim 21 wherein the tubing is formed of acrylic.

27. A method of determining matric potential of a sample, the method comprising:

providing a tensiometer including a porous member configured to contact an upper surface of a sample, a fluid chamber above the porous member and in fluid communication with the porous member, a pressure transducer in fluid communication with the fluid chamber, tubing having opposite open ends, a connector coupling one of the open ends of the tubing to the fluid chamber, and a septum on the other end of the tubing;

filling the chamber with a liquid; and contacting a surface of a sample with the porous member and insulating the sample and at least a portion of the tensiometer, which portion includes the porous member, against the ambient.

28. A method of determining matric potential of a sample in accordance with claim 27 wherein said insulating comprises wrapping the sample and tensiometer with a flexible impermeable film.

* * * * *